United States Patent [19]

van den Ouweland

[11] 3,950,565

[45] Apr. 13, 1976

[54] FLAVORING FOODS

[75] Inventor: Godefridus Antonius Maria van den Ouweland, Zevenaar, Netherlands

[73] Assignee: Lever Brothers Company, New York, N.Y.

[22] Filed: July 11, 1973

[21] Appl. No.: 378,085

[30] Foreign Application Priority Data
July 12, 1972 United Kingdom............... 32653/72

[52] U.S. Cl............................... 426/536; 260/347.8
[51] Int. Cl.$^2$....................................... A23L 1/226
[58] Field of Search...................... 426/65, 175, 536

[56] References Cited
UNITED STATES PATENTS

| | | | |
|---|---|---|---|
| 3,455,702 | 7/1969 | Willhalm et al. | 426/175 X |
| 3,697,291 | 10/1972 | Tonsbeek | 426/65 |
| 3,709,697 | 1/1973 | de Groot et al. | 426/65 |

*Primary Examiner*—Joseph M. Golian
*Attorney, Agent, or Firm*—Kenneth F. Dusyn; James J. Farrell; Arnold Grant

[57] ABSTRACT

Addition compounds of 2- or 5-monoalkyl and 2,5-dialkyl-4-hydroxy-2,3-dihydrofuran-3-ones and $C_2$-$C_9$ carbonyl compounds are provided. These addition compounds are useful to impart improved flavouring properties to foodstuffs.

5 Claims, No Drawings

FLAVORING FOODS

BACKGROUND OF THE INVENTION

It has been proposed to incorporate certain furenidones, i.e. 4.hydroxy-2,3-dihydrofuran-3-ones with two alkyl substituents in the 2- and 5-positions, into foodstuffs in order to improve their flavouring properties. It was found, however, that these compounds are not quite stable under certain conditions. The problem arises particularly when foodstuffs containing the furenidone, in particular a 2,5-dialkylfurenidone, are stored for a prolonged time or when heating when preparing the foodstuff is necessary.

SUMMARY OF THE INVENTION

The invention relates to a chemical process for preparing novel chemical compounds, to the compounds per se and a process for improving the flavouring characteristics of foodstuffs by incorporating the novel compounds and to the foodstuffs thus obtained.

It has now been found that addition compounds of mono- or dialkylfurenidones and carbonyl compounds such as aldehydes and ketones can be conveniently prepared and that these compounds - which are stable upon storage - under suitable conditions, especially upon heating, revert to the free furenidone and that they therefore are excellent precursors of the furenidones which can advantageously be incorporated in foodstuffs.

DETAILED DESCRIPTION

The flavour precursors of the present invention are derived from a furenidone and a carbonyl compound, both of which possess valuable flavouring properties.

The nature of the carbonyl compound determines whether the precursor reverts under mild or under more severe conditions to the flavouring furenidone.

Under acid or neutral reaction conditions the following addition reaction of the furenidone takes place:

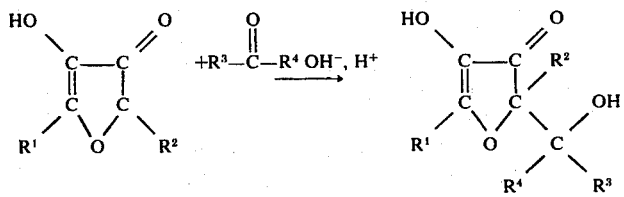

In this general formula $R^1$ and $R^2$ represent a lower $C_1$-$C_4$ alkyl group, preferably methyl or ethyl, while $R^3$ represents hydrogen or a methyl group and $R^4$ represents hydrogen or an organic radical consisting of 1–14 carbon atoms, hydrogen and 0–2 oxygen atoms, preferably a hydrocarbyl, more in particular an alkyl group or alkenyl group containing 2–10 carbon atoms. Furthermore, in case $R^3$ represents a methyl group, $R^4$ should not contain more than 4 carbon atoms. These novel carbonyl addition compounds occur in two stereoisomeric forms in case $R^3$ and $R^4$ represent different groups and both forms are suitable flavour precursors for the purpose of this invention.

Particularly preferred carbonyl compounds which can be added to the furenidone are aliphatic saturated and unsaturated aldehydes and methyl-ketones such as acetaldehyde propanal, octanal, acetone, methylethylketone, cis-3-hexenal and cis-4-heptenal. Aromatic and heterocyclic aldehydes such as phenylacetaldehyde, benzaldehyde, furfuraldehyde, methylfurfuraldehyde and hydroxymethylfurfuraldehyde, can also be used. Carbonyl compounds containing 6–8 carbon atoms are preferred.

The addition reaction takes place smoothly in a suitable polar solvent such as water in the presence of an acid-base catalyst under neutral or acid conditions at room temperature although higher - up to 100°C - and lower temperatures, above 5°C, can also be used. Atmospheric pressures are suitably employed. However, too high temperatures favour reversion.

The novel addition compounds of the alkyl substituted furenidones can be isolated without undue difficulties and may be used according to the present invention for incorporation into foodstuffs, in particular in foodstuffs which are heated to temperatures over 100°C when being prepared for consumption. Such foodstuffs are e.g. shortenings, fats, margarines, especially bakery frying margarines, dried sterilised or deepfrozen soups, meat products, meatballs, ready-made meals, meat imitating products such as those known as texturised vegetable protein, mesophase, and various products used in bakeries, e.g. reinforced flour, baking aids etc. The amount of addition compound incorporated into the foodstuff ranges from 0.1–500 parts per million, dependent on the particular precursor and foodstuff, preferably 1–100 ppm.

Incorporation into the product may take place by adding the addition compound to the ingredients, spraying over the formed products etc. The addition compounds are usually used in conjunction with further flavouring agents or precursors thereof, such as e.g. amino acids, nucleotides, carboxylic acids, sweetening substances, etc. Of course the actual combination is determined by the type of product.

By way of illustration the following Examples are given to elucidate the invention:

EXAMPLE I 2-(1-hydroxyethyl)-2,5-dimethyl-4-hydroxy-3-(2H)-furanone was prepared as follows:

In a round-bottomed flask equipped with a stirrer and a condensor, 12.8 g (0.1 mole) of 2,5-dimethyl-4-hydroxy-3-(2H)-furanone and 44 g (1.0 mole) of acetaldehyde were introduced into a solution of 3.0 g of oxalic acid in 100 ml of water. The mixture was stirred and refluxed for 1 hour. After cooling, the mixture was extracted 5 times with 25 ml portions of chloroform and the organic solvent was evaporated off. The residue was purified by chromatography on 50 g of polyamide. After elution by means of a 50/50 mixture of ether and petroleum ether, 9.4 g of the title compound was obtained (which corresponds to a yield of 54%). Recrystallization from ether gave the pure product with m.p. 112–114°C).

Infrared absorptions (in KBr disc.) were at 3400, 3200, 1697, 1610, 1450, 1370, 1250, 1072, 1066, 1005 and 924 cm$^{-1}$.

The NMR spectrum [in CDCl$_3$, internal standard Si(CH$_3$)$_4$] had signals at $\delta = 1.17$ (doublet), $\delta = 1.41$ (singlet), $\delta = 2.27$ (singlet), $\delta = 3.81$ (quartet), 4.3–5.7 (broad peak).

The mass spectrum showed peaks at m/e 172, 157, 155, 154, 128, 101, 85, 83, 72, 45, 43.

50 mg of the compound thus obtained was heated in 0.5 ml of water to a temperature of 100°C. The breakdown of the compound into 2,5-dimethyl-4-hydroxy-3-(2H)-furanone and acetaldehyde was followed by investigating the n.m.r. signals at intervals. In particular the diminishing signal of the starting compound at 0.99 ppm (with respect to dimethylsulfoxide) and the increasing signals of 2,5-dimethyl-4-hydroxy-3-(2H)-furanone at 1.25 and 2.08 ppm were followed. The other signals present in the spectrum recorded in CDCl$_3$ solution are obscured by the water signal. From the change in signals it was deduced that after about 48 hours 50% of the starting material had been converted into the 2,5-dimethyl-4-hydroxy-3-(2H)-furanone. In an aprotic solvent 50% was converted within a fraction of an hour to 24 hours, as a similar experiment showed, whereas at 160°C 50% was converted in ¼ hour.

EXAMPLE II 2-(1-hydroxybenzyl)-2,5-dimethyl-4-hydroxy-3-(2H)-furanone was prepared as follows:

A mixture of 5 g of 2,5-dimethyl-4-hydroxy-3-(2H)-furanone and 10.6 g of benzaldehyde was added to a mixture of 20 ml of water, 20 ml of dioxan and 0.5 g of oxalic acid. The mixture was then refluxed for 4 hours, cooled and extracted with chloroform. The chloroform extract was evaporated and the residue purified by column chromatography over polyamide using ether - light petroleum 50/50 as the eluent; 2.7 g (30% yield) of the title compound was obtained which was recrystallized from chloroform, m.p. = 122°–124°C.

Infrared absorptions (KBr disc.) were at 3400, 1715, 1635, 1455, 1370, 1240, 1096, 1080, 1042, 1010, 910 and 705 cm$^{-1}$. The NMR spectrum [solvent CDCl$_3$, internal standard Si(CH$_3$)$_4$] had signals at $\delta = 1.22$ (singlet), $\delta = 2.17$ (singlet), $\delta = 4.73$ (singlet), $\delta = $ 4.9–5.6 (broad peak), $\delta = 7.15$ (singlet).

The mass spectrum showed peaks at m/e 234, 128, 107, 106, 105, 85, 77, 57, 55, 52, 51, 50, 45, 43.

EXAMPLE III 2-(1-hydroxy-2-phenylethyl)-2,5-dimethyl-4-hydroxy-3-(2H)-furanone was prepared as follows:

To a mixture of 6 g (0.05 mole) phenylacetaldehyde and 1.28 g (0.01 mole) of 2.5-dimethyl-4-hydroxy-3-(2H)-furanone was added 60 mg of boric acid and the mixture was stirred at 80°C for 3 hours. After working up the reaction mixture as described earlier, 0.57 g (23%) of the title compound was obtained, with melting point 157.5°–159°C.

Infrared absorptions (KBr disc.) were at 3500, 3240, 1697, 1616, 1447, 1298, 1240, 1097, 1058, 746 and 703 cm$^{-1}$. The NMR spectrum [solvent DMSO-d6 + CDCl$_3$ (3:2), internal standard Si(CH$_3$)$_4$] had signals at $\delta = 1.32$ (singlet), $\delta = 2.15$ (singlet), $\delta = 2.35$–2.62 (multiplet), $\delta = 3.60$ (multiplet), $\delta = 5.00$ (doublet), $\delta = 7.00$ (singlet), $\delta = 7.98$ (singlet).

The mass spectrum showed peaks at m/e 248, 230, 205, 157, 128, 121, 120, 111, 103, 101, 91, 77, 43. The addition compound in an aprotic solvent was converted for 50% to 2.5-dimethyl-4-hydroxy-3-(2H)-furanone after heating for ⅓ hour at 160°C.

EXAMPLE IV 0.3 g of 2-(1-hydroxyethyl)-2,5-dimethyl-4-hydroxy-3-(2H)-furanone was added to 1000 g of unflavoured margarine and the mixture then heated in a pan for 5 minutes at 160°–170°C. This flavoured fried margarine was preferred to a fried margarine without addition by 8 out of 11 tasters, who mentioned particularly its sweet, caramel-like aroma.

EXAMPLE V

To 100 g of hardened fat 5 mg of 2-(1-hydroxyethyl)-2,5-dimethyl-4-hydroxy-3-(2H)-furanone was added and the mixture was then heated for 5 minutes at 150°C. This fat was preferred to a fat without addition by 9 out of 10 tasters who mentioned particularly its mild fruity aroma.

EXAMPLE VI

A basis for canned beef soup was prepared by adding the following ingredients to 4 liters of water:

|  | grams |
|---|---|
| Noodles | 160 |
| Herb and spices | 1.6 |
| Tallow | 80 |
| Vegetables | 400 |
| Monosodium glutamate | 16 |
| Protein hydrolysate | 16 |
| Meat extract | 16 |
| Salt | 64 |
| Raw meat | 400 |

The total amount was divided into two portions of each 2 liters; 0.08 g of 2-(1-hydroxyethyl)-2,5-dimethyl-4-hydroxy-3-(2H)-furanone was added to one of the portions. The second portion, which was used without further addition, served as a comparative example. The mixtures thus obtained were canned in half liter tins and sterilised in an autoclave for 1 hour at 120°C. A soup ready for consumption was prepared by adding an equal volume of water to the contents of each tin. After heating the soups were tested and a majority of the flavour evaluation panel preferred the soup with the added flavour precursor because of its more pronounced meaty flavour.

EXAMPLE VII

A shortcake dough was prepared with the following ingredients:

|  | grams |
|---|---|
| Flour | 450 |
| Sugar | 225 |
| Fat | 250 |
| Water | 65 |
| Salt | 5 |
| Baking powder | 3 |

The fat and the sugar were mixed in a Hobart mixer (Type: CE 100) for 3 minutes at speed 2. After adding the water, mixing proceeded for another 2 minutes. Subsequently the flour, the salt and the baking powder were added, after which the composition was mixed for 10 minutes. The dough was spouted on baking trays in the shape of piped shortcakes and baked for 20 minutes at 180°C. In an analogous way piped shortcakes were prepared in which, however, 20 mg of 2-(1-hydroxy-2-phenylethyl-2,5-dimethyl-4-hydroxy-3-(2H)-furanone were added to the dough. The shortcakes thus prepared were evaluated by a panel in a pair test. The shortcakes to which 2-(1-hydroxy-2-phenylethyl-2,5-dimethyl-4-hydroxy-3-(2H)-furanone had been added were generally preferred by the members of the panel.

EXAMPLE VIII

A mixture of 10 g of 2,5-dimethyl-4-hydroxy-3-(2H)-furanone, 20 ml of a 37% formaldehyde aqueous solution, 50 ml of water and 0.7 g of oxalic acid was stirred for 18 hours at room temperature. After working up the reaction mixture, the crude reaction product was purified by column chromatography over polyamide. Elution with pentane-dichloromethane 80/20 yielded the pure 2-hydroxymethyl-2,5-dimethyl-4-hydroxy-3-(2H)-furanone, which was recrystallized from ethyllactate; m.p. 124°–125°C.

Infrared absorptions (KBr disc.) were at 3360, 3170, 1693, 1675, 1607, 1596, 1465, 1300, 1280, 1236, 1220, 1160, 1085, 1050, 1000, 950, 905, 850, 770, 605, 552, 506 and 397 $cm^{-1}$.

NMR spectrum [DMSO-d6 (dimethylsulfoxide, containing 6 deuterium atoms instead of hydrogen), internal standard $Si(CH_3)_4$] had signals at $\delta = 1.25$ (singlet), $\delta = 2.13$ (singlet), $\delta = 3.42$ (broad signal), $\delta = 5.0$ (broad signal), $\delta = 8.1$ (broad signal).

The mass spectrum showed peaks at m/e 158, 141, 140, 128, 127, 115, 101, 97, 85, 69, 43.

EXAMPLE IX

To a mixture of 1.0 g of 2,5-dimethyl-4-hydroxy-3-(2H)-furanone, 5 g of propanal and 20 ml of water were added 0.2 g of oxalic acid and the mixture was stirred at room temperature for 25 hours and then extracted three times with chloroform. The chloroform extract was evaporated and the residue purified by column chromatography on polyamide using ether-pentane 10/90 as the eluent. Pure 2-(1-hydroxypropyl)-2,5-dimethyl-4-hydroxy-3-(2H)-furanone was obtained, which was recrystallized from ether-pentane 50/50; solid mass at room temperature.

Infrared absorptions (KBr disc.) were at 3380, 3200, 1695, 1617, 1460, 1440, 1380, 1370, 1365, 1295, 1254, 1215, 1084, 1078, 1009, 973, 948, 731 and 570 $cm^{-1}$.

NMR spectrum [DMSO-d6, internal standard $Si(CH_3)_4$] had signals at $\delta = 1.25$ (singlet), $\delta = 2.10$ (singlet), $\delta = 3.26$ (multiplet), $\delta = 4.92$ (doublet), $\delta = 8.03$ (singlet), $\delta = 1.25$ (multiplet), $\delta = 0.90$ (multiplet).

The mass spectrum showed peaks at m/e 186, 157, 128, 101, 97, 85, 69, 57, 43.

EXAMPLE X

Example IX was repeated except that in this instance the propanal was replaced by 5 g of butanal. From the reaction mixture 2-(1-hydroxybutyl)-2,5-dimethyl-4-hydroxy-3-(2H)-furanone was isolated with m.p. 103°–104.5°C.

Infrared absorptions (KBr disc.) were at: 3490, 3150, 1690, 1618(sh), 1609, 1462, 1435, 1365, 1340, 1272, 1245, 1222, 1090(sh), 1075, 1050, 1005, 982, 948, 855, 760, 745, 720, 689, 607, 595 and 586 $cm^{-1}$.

NMR spectrum [DMSO-d6, internal standard $Si(CH_3)_4$] had signals at: $\delta = 1.20$ (singlet), $\delta = 2.05$ (singlet), $\delta = 3.30$ (multiplet), $\delta = 4.82$ (doublet), $\delta = 7.85$ (singlet), $\delta = 1.0$–$1.5$ (multiplet), $\delta = 0.80$ (triplet).

The mass spectrum showed peaks at m/e 200, 157, 139, 128, 111, 101, 85, 72, 71, 57, 43.

EXAMPLE XI

Example IX was repeated, except that in this instance the propanal was replaced by 6 g of octanal. From the reaction mixture 2-(1-hydroxyoctyl)-2,5-dimethyl-4-hydroxy-3-(2H)-furanone was isolated with melting point 97°–98°C.

Infrared absorptions were at (KBr disc.): 3495, 3180, 2960, 2920, 2860, 1690, 1618, 1610, 1460, 1436, 1365, 1335, 1260, 1245, 1205, 1070, 1005, 972, 945, 760, 722 and 578 $cm^{-1}$.

NMR spectrum [solvent DMSO-d6, internal standard $Si(CH_3)_4$] had signals at: $\delta = 1.25$ (singlet), $\delta = 2.10$ (singlet), $\delta = 3.30$ (multiplet), $\delta = 4.93$ (doublet), $\delta = 8.00$ (singlet), $\delta = 1.20$ (multiplet), $\delta = 0.85$ (triplet).

The mass spectrum showed peaks at m/e 256, 195, 167, 130, 129, 128, 85, 84, 82, 81, 57, 43.

EXAMPLE XII

Example IX was repeated, except that in this case the propanal was replaced by 4 g of cis-4-heptenal. After column chromatography of the reaction mixture the pure 2-(1-hydroxy-4-cis-heptenyl)-2,5-dimethyl-4-hydroxy-3-(2H)-furanone was isolated.

Infrared absorptions (KBr disc.) at: 3480, 3200, 3005, 1695, 1615, 1458, 1435, 1370, 1336, 1249, 1240, 1083, 1070, 1004, 935, 760, 720, 685 and 575 $cm^{-1}$.

NMR spectrum [solvent DMSO-d6, internal standard $Si(CH_3)_4$] had signals at: $\delta = 1.21$ (singlet), $\delta = 2.05$ (singlet), $\delta = 3.40$ (multiplet), $\delta = 4.90$ (broad signal), $\delta = 7.90$ (broad signal), $\delta = 1.2$–$1.5$ (multiplet), $\delta = 1.7$–$2.2$ (multiplet), $\delta = 5.15$ (multiplet), $\delta = 0.89$ (triplet).

The mass spectrum showed peaks at m/e 240, 222, 179, 151, 129, 128, 95, 85, 84, 83, 69, 68, 57, 55, 43.

EXAMPLE XIII

Example IX was repeated, except that in this instance the propanal was replaced by 5 g of furfural. From the reaction mixture 2-(1-hydroxymethylfuran)-2,5-dimethyl-4-hydroxy-3-(2H)-furanone was isolated by column chromatography as a mixture of two dia stereoisomers in the form of a semi-solid mass at room temperature.

Infrared absorptions (KBr disc.) were at: 3440, 3200, 1700, 1617, 1500, 1450, 1370, 1239, 1145, 1074, 1050, 1005 and 740 $cm^{-1}$.

NMR spectrum [solvent DMSO-d6, internal standard $Si(CH_3)_4$] had signals at: $\delta = 1.05$ and $1.35$ (singlet), $\delta = 2.02$ and $2.14$ (singlet), $\delta = 4.52$ and $4.57$ (singlet), $\delta = 5.50$ and $5.80$ (broad signal), $\delta = 8.00$ (broad signal), $\delta = 6.1$–$6.4$ (multiplet), $\delta = 7.35$ and $7.50$ (quartet).

The mass spectrum showed peaks at m/e 224, 128, 127, 97, 96, 95, 85, 57, 43.

EXAMPLE XIV

A mixture of 2.0 g of 2,5-dimethyl-4-hydroxy-3-(2H)-furanone, 10 ml of acetone and 25 ml of 6N hydrochloric acid was stirred at room temperature for 48 hours. After working up the reaction mixture, the crude reaction product was purified by column chromatography. Elution with pentane-ether 90/10 yielded pure 2-(2-hydroxy-2-propyl)-2,5-dimethyl-4-hydroxy-3-(2H)-furanone.

Infrared absorptions were at (KBr disc.): 3480, 3380, 1700, 1686, 1620(sh), 1610, 1470, 1460, 1445, 1383, 1370, 1256, 1210, 1182, 1118, 1080, 1075, 1003, 969, 902, 860, 794, 750, 565, 325 and 318 cm$^{-1}$.

NMR spectrum [solvent DMSO-d6, internal standard Si(CH$_3$)$_4$] had signals at: $\delta = 0.99$ (singlet), $\delta = 1.12$ (singlet), $\delta = 1.18$ (singlet), $\delta = 2.05$ (singlet), $\delta = 4.32$ (singlet), $\delta = 7.80$ (broad signal).

The mass spectrum showed peaks at m/e 186, 171, 129, 127, 101, 97, 85, 71, 59, 58, 57, 43. In an aprotic solvent the compound was fully converted to the furenidone upon heating at 160°C for 8 minutes.

EXAMPLE XV

To 200 g or a commercial available frying fat were added 15 mg of 2-(1-hydroxy-4-cis-heptenyl)-2,5-dimethyl-4-hydroxy-3-(2H)-furanone and the mixture was heated for 5 minutes at 150°C. This fat was unanimously preferred to the fat without addition by the flavour evaluation panel, because of its more sweet, butterlike character.

What is claimed is:

1. A foodstuff that is heated to a temperature of over 100°C when prepared for consumption comprising 0.1–500 parts per million of a compound of the formula:

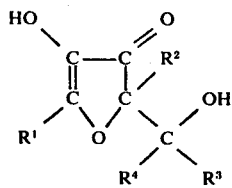

in which R$^1$ and R$^2$ represent a C$_1$–C$_4$ alkyl group, R$^3$ represents hydrogen or a methyl group and R$^4$ represents hydrogen, an alkyl group containing 1–14 carbon atoms or an alkenyl group containing 2–10 carbon atoms provided that R$^4$ does not contain more than 4 carbon atoms when R$^3$ is a methyl group.

2. A foodstuff according to claim 1, comprising 1–100 parts per million of the compound.

3. A method of improving the flavoring characteristics of foodstuffs that are heated to temperatures over 100°C when prepared for consumption, in which 0.1 to 500 parts per million of a compound of the formula:

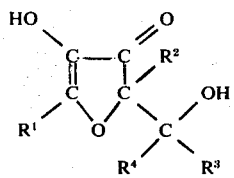

in which R$^1$ and R$^2$ represent a C$_1$–C$_4$ alkyl group, R$^3$ represents hydrogen or a methyl group and R$^4$ represents hydrogen, an alkyl group containing 1–14 carbon atoms or an alkenyl group containing 2–10 carbon atoms provided that R$^4$ does not contain more than 4 carbon atoms when R$^3$ is a methyl group, is incorporated into said foodstuff.

4. A method according to claim 3, in which 1 to 100 parts per million of said compound is incorporated into said foodstuff.

5. A foodstuff that is heated to a temperature of over 100°C when prepared for consumption comprising 0.1–500 parts per million of a compound selected from the group consisting of:
   (a) 2-(1-hydroxyethyl)-2,5-dimethyl-4-hydroxy-3-(2H)-furanone;
   (b) 2-(1-hydroxybenzyl)-2,5-dimethyl-4-hydroxy-3-(2H)-furanone;
   (c) 2-(1-hydroxy-2-phenylethyl)-2,5-dimethyl-4-hydroxy-3-(2H)-furanone;
   (d) 2-hydroxymethyl-2,5-dimethyl-4-hydroxy-3-(2H)-furanone;
   (e) 2-(1-hydroxypropyl)-2,5-dimethyl-4-hydroxy-3-(2H)-furanone;
   (f) 2-(1-hydroxybutyl)-2,5-dimethyl-4-hydroxy-3-(2H)-furanone;
   (g) 2-(1-hydroxyoctyl)-2,5-dimethyl-4-hydroxy-3-(2H)-furanone;
   (h) 2-(1-hydroxy-4-cis-heptenyl)-2,5-dimethyl-4-hydroxy-3-(2H)-furanone;
   (i) 2-(1-hydroxymethylfuran)-2,5-dimethyl-4-hydroxy-3-(2H)-furanone; and
   (j) 2-(2-hydroxy-2-propyl)-2,5-dimethyl-4-hydroxy-3-(2H)-furanone.

* * * * *